United States Patent [19]
Baritiu et al.

[11] Patent Number: 4,717,547
[45] Date of Patent: Jan. 5, 1988

[54] APPARATUS FOR ADJUSTING THE AMINE LOAD UPON A COLUMN FOR SCRUBBING NATURAL GAS

[75] Inventors: Georges-Michel Baritiu, Versailles; Jean-Claude Gherardi; Bernard Leconte, both of Artix, all of France

[73] Assignee: Societe Nationale Elf Aquitaine (Production), Courbevoie, France

[21] Appl. No.: 811,777

[22] Filed: Dec. 20, 1985

[30] Foreign Application Priority Data

Dec. 21, 1984 [FR] France .................. 84 19616

[51] Int. Cl.$^4$ .................. G01N 21/05; B01J 10/00
[52] U.S. Cl. .................. 422/62; 422/168; 423/228; 436/55; 356/246
[58] Field of Search .................. 356/410, 246; 422/62, 422/168; 436/55; 423/228, 229, 243

[56] References Cited

U.S. PATENT DOCUMENTS

| | | | |
|---|---|---|---|
| 3,685,960 | 8/1972 | Benson | 423/229 |
| 3,690,816 | 9/1972 | Alleman | 423/228 |
| 3,810,695 | 5/1974 | Shea | 356/73 |
| 4,256,695 | 5/1981 | Gillespie | 422/62 |
| 4,260,257 | 4/1981 | Neeley et al. | 356/410 |
| 4,286,965 | 9/1981 | Vanhumbeeck et al. | 422/82 |
| 4,326,806 | 4/1982 | Donner | 356/410 |
| 4,614,428 | 9/1986 | Harris et al. | 356/246 |

Primary Examiner—Michael S. Marcus
Attorney, Agent, or Firm—Oblon, Fisher, Spivak, McClelland, & Maier

[57] ABSTRACT

A process and apparatus for adjusting the amine load upon an absorption column for the desulfuration of gases uses a photometric cell allowing measurements of absorption to be taken, wherein the process comprises performing the said adjustment as a function of the residual content in the amine of the gas to be eliminated, the sample being drawn off in liquid phase from inside the column. The application of said process to the processing of natural acid gases is disclosed together with an embodiment of a photometer cell.

4 Claims, 2 Drawing Figures

APPARATUS FOR ADJUSTING THE AMINE LOAD UPON A COLUMN FOR SCRUBBING NATURAL GAS

BACKGROUND OF THE INVENTION

1. Field of the Invention

The present invention concerns a novel process for adjusting the amine load upon an absorption column intended for the disulfuration of gas, taking into account the absorption rate of the gas to be eliminated on the amine. It also concerns a device which reduces to practice the process and in particular the photometric cell that allows measurements.

2. Description of the Prior Art

Scrubbing using amine, of gas containing hydrogen sulfide is well known to the man skilled in the art. According to this process, the gas to be scrubbed is injected into the bottom of an absorption column, in which it is contacted at counter-current with an amine solution. The scrubbed gas is recovered at the head of the column and the amine loaded with hydrogen sulfide exits at the bottom of the column, in order to be regenerated and reinjected into the absorption column.

The problem that arises is that of controlling the amine flow-rate taking into account operating conditions. It is possible, as disclosed in French Pat. No. 2,141,413, to control the mass flow-rate of the amine solution to the mass flow-rate of the gas to be scrubbed. It is also possible, as disclosed in U.S. Pat. No. 3,288,706 to analyze the gas at the output of the absorption column (once scrubbed) or the saturated amine at the bottom of the column.

These different control and adjustment methods present the principal drawback of being based upon parameters that are external to the column, namely:

in particular for the first above-mentioned patent, the process is based on elements existing prior to the reaction per se and thus is not able to take into account the behavior per se of the reaction;

for the second above-mentioned patent, the process is based on observing subsequently the result of the reaction and thus on reacting with a lapse of time.

These parameters do not take into account an eventual loss of adjustment or an overload on the column, due to a discrepancy of the measurements with respect to the absorption reactions and/or to a lack of precision and to the variable response time of the equipment.

SUMMARY OF THE INVENTION

The present invention aims overcoming these drawbacks. In order to do this, it foresees a process for controlling the amine load, wherein the said control is performed as a function of the residual content in the amine of the gas to be eliminated, the sample being drawn off in the liquid phase inside the column.

The invention also provides an installation for reducing to practice this process and comprising: a device for the continuous drawing off of the amine sample, a circuit for introducing the amine and a system for controlling the amine flow-rate.

The analyzing circuit acts upon the amine load circuit as a function of the rate of absorption of the gas to be eliminated on the amine.

Another characteristic of the invention is that the analyser comprises a photometer, the measuring cell of which is capable of withstanding high pressures and temperatures with a very short and adjustable optical trajectory. It is thus possible to analyze the amine upon which is absorbed the hydrogen sulfide within the core itself of the column.

The advantages obtained due to this invention are of considerable importance. In the first place, the in situ measuring of the H2S absorption rate on the amine allows control of the amine load at the exact moment when the reaction deviates from a predetermined rate. In particular, in this way all risks of flare are prevented, or at least their frequency is reduced. Furthermore, a quasi-perfect stability of operating is obtained, thereby producing a saving in energy on the pumping of the load, on the one hand, and on the regenerating of the amine, on the other hand.

According to one characteristic of the invention, it is possible to complete this adjustment or control by associating thereto a recording of the temperatures throughout the length of the absorber and to associate an adjustment a priori through an electronic device for the economic management or control of the process.

BRIEF DESCRIPTION OF THE DRAWINGS

The invention will become more apparent from reading the following embodiment, given by way of non-limiting illustration with reference to the appended drawings in which.

DETAILED DESCRIPTION OF THE PREFERRED EMBODIMENT

Figure 1:
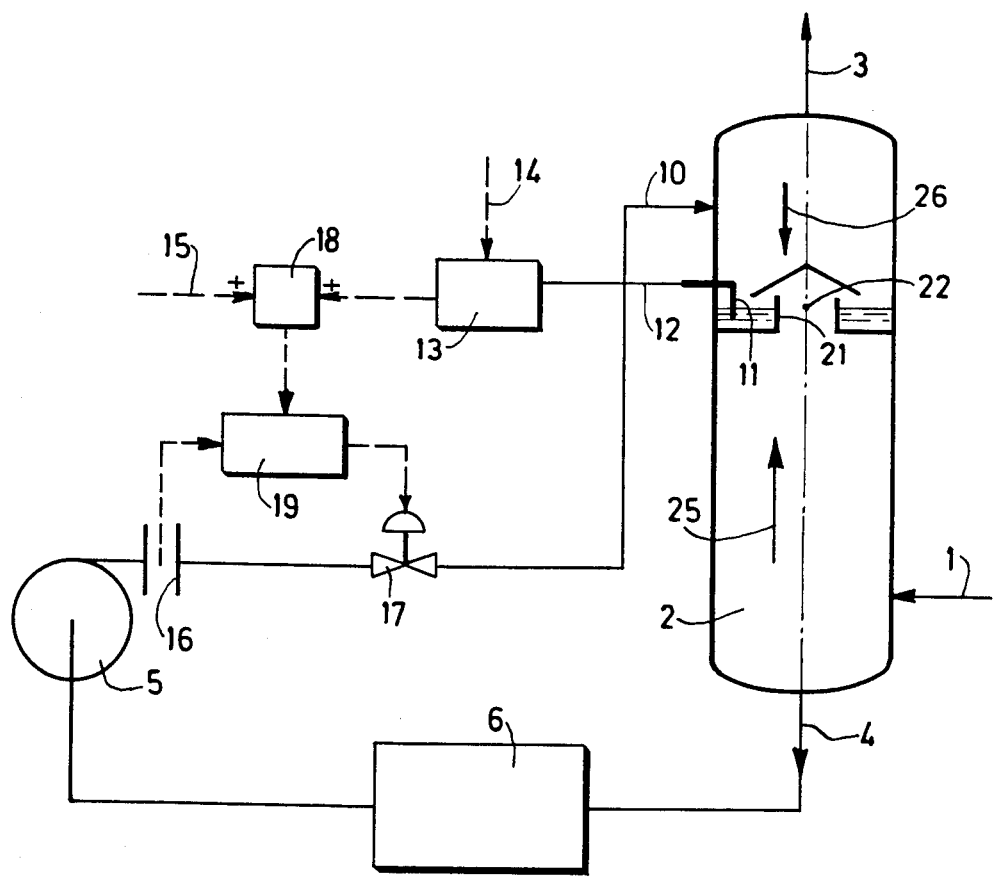
FIG. 1 partially represents a desulfuration installation produced according to the invention.

FIG. 1 represents an installation for the desulfurization of gases comprising an absorber 2, load or evacuation pipes 1, 3, 4 and 10, an amine load pump 5, a regeneration unit 6, a tapping device 11 and a control system constituted by the analyzer 13, the addition module 18 and regulator 19, a flow-rate meter 16 and an automatic valve 17.

With reference to FIG. 1 the gas to be scrubbed 25 containing hydrogen sulfide and possibly other acid compounds arrives through the pipe 1 and enters the bottom of an absorber 2 in which it is contacted at counter-current with a concentrated hot amine solution 26 introduced through pipe 10. The scrubbed gas issues at the head of the absorber through the pipe 3 and the amine solution, having fixed the acid compounds, is brought through the intermediary of the pipe 4 to a regeneration unit 6. Once the amine has been regenerated, it is re-pumped by the load pump 5 in order to be thereafter reinjected into the absorber.

For the control of the amine flow-rate, a tapping 11 is performed, issuing into the liquid phase 21 at the level 22 of one of the baffle plates of the absorber. The sample is then brought through the intermediary of a pipe in which a safety system with respect to the pressure towards the analyser 13 has been foreseen. The said analyser comprises a photometer, the cell of which is adapted to withstand very high pressures and temperatures and allows the taking of measurements upon very short and adjustable optical trajectories. The measurement, after adjustable amplification, of the saturation rate of the amine is compared to a previously determined reference 14 and modifies by increasing or decreasing it, an outflow reference 15, due to an addition module 18. The output signal of the module 18 is piloting the reference point of the control-loop of the flow-rate constituted by the flow-rate meter 16, the regulator 19 and the automatic valve 17.

Furthermore, so as to confirm the evolution of the measurement given by the analyser 13, it is possible to perform a follow-up of the temperatures taken on one or several baffle plates, still in the liquid phase, thereby allowing visualization of the displacement of the absorption front within the column.

Another embodiment for the control of the amine flow-rate consists in acting not upon the valve 17 but upon the speed of the pump 5, for example, by controlling the steam admission of a driving turbine or the speed of an electric motor through any suitable means.

Figure 2:
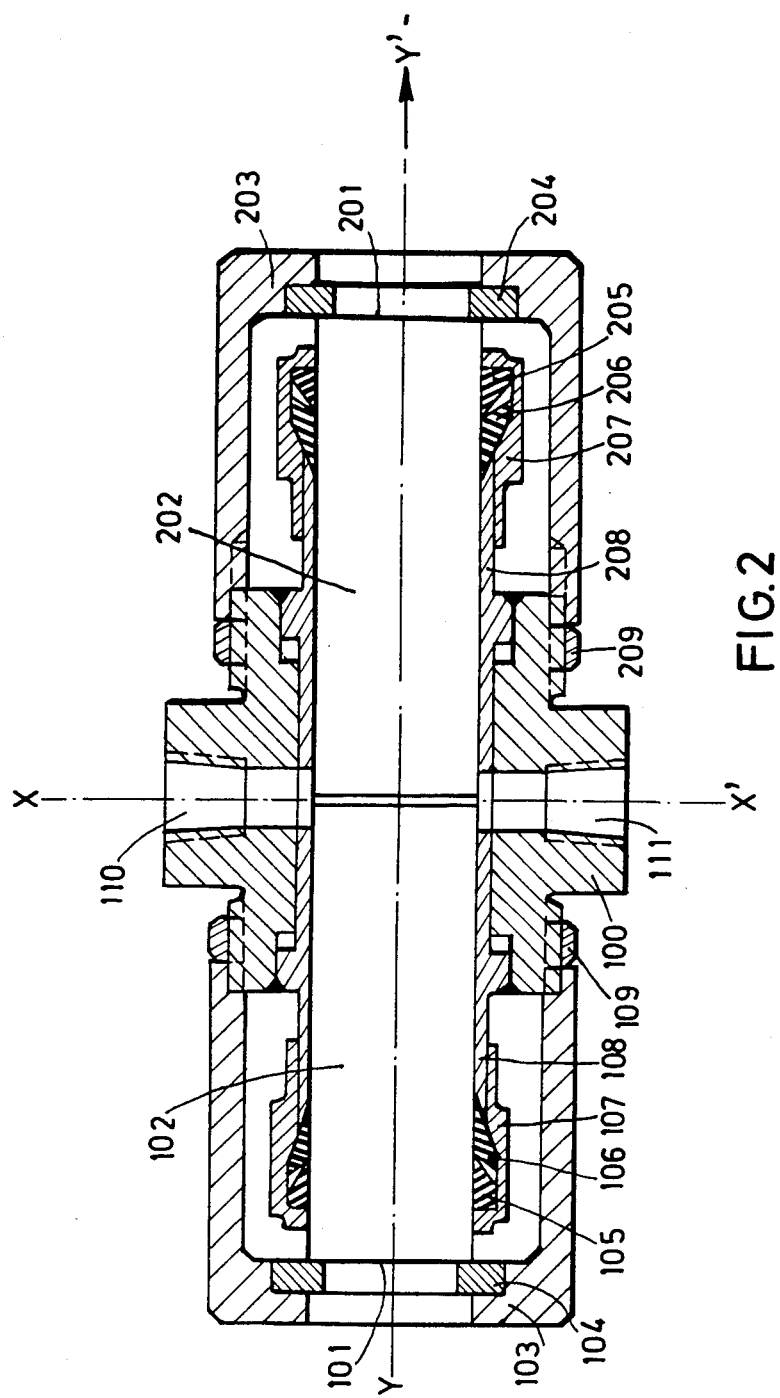
FIG. 2 is a detailed cross-section of a photometer cell for use in the apparatus of FIG. 1.

The resulting device, such as described herein-above, can only be envisaged with a measuring system, especially adapted to withstand high pressures and temperatures and which allows very short optical trajectories, since large quantities of hydrogen sulfide absorbed on the amine, and not traces, have to be analyzed. Furthermore, the optical trajectory must be easily adjustable in order to be able to adapt the sensitivity of the analysis to the characteristics of the column. FIG. 2 represents a preferred embodiment of a photometric cell that meets these requirements.

With reference to FIG. 2, the photometer cell is symmetrical with respect to a plane passing through the axis XX' and perpendicular to the optical axis YY'. It also presents a revolution symmetry around the axis YY'. The cell comprises two quartz cylinders 102 and 202, their diameters corresponding to the internal diameters of two bodies 108 and 208, themselves packed and welded within the internal cylindrical recess of a main body 100. On each of these bodies 108 and 208, is screwed a socket 107 (respectively 207) by wedging against the corresponding quartz cylinder a joint or seal 105 (respectively 205) and a joint 106 (respectively 206) having a bevelled form. The tip of the bevelled portion of the said joint 106 (respectively 206) is wedged between the quartz and the end of the body 108 (respectively 208) that is cut in a bevelled form in the opposite direction. Similarly, the tip of the bevelled portion of the joint 105 (respectively 205) is wedged between the quartz and the other end of the joint 106 (respectively 206) that is shaped in a bevelled form in the opposite direction. These joints 105 and 106 (respectively 205 and 206) are made of polytetrafluoroethylene (PTFE) and ensure the sealing to pressure. Since the two quartz cylinders are positioned in such a manner as to obtain the desired optical trajectory (interquartz distance), their positions are fixed through tightening of the sockets 107 and 207 upon the bodies 108 and 208 after introduction of a wedge of a suitable thickness through one of the orifices 110 or 111. This sealing is completed by a ring made of polytetrafluoroethylene 104 (respectively 204) that is applied against the bottom of the quartz cylinder 101 (respectively 201) through screwing of the base 103 (respectively 203) upon the main body. This screwing is rendered fool-proof by blocking in counter-bolt 109 against the base 103.

A perfect sealing to pressure and to temperature is thus obtained with as short an optical trajectory as desired. The product to be analyzed enters through the hole 110 having axis XX' and provided in the main body, passes between the two quartz cylinders that determine the optical trajectory and exits through the hole 111 also of axis XX'.

The present invention is in no way limited to the single embodiment described herein-above and can, on the contrary encompass all variants.

In particular, it is possible to envisage insulating the photometric installation, in the case of leakages or adjustment of the cell. In order to do this, it is possible to utilize a system of valves that short-circuit the inlet and the outlet of the photometer and of which the action will be actuated automatically, for example, upon the appearance of a leakage.

We claim:

1. Apparatus for scrubbing natural gas of an undesirable component, comprising:
    an absorption column having a natural gas inlet and a natural gas outlet spaced therefrom and so disposed that a flow of natural gas may be established through said column, said absorption column further having an amine inlet and an amine outlet spaced therefrom and so disposed that a flow of amine may be established through said column and in contact with said flow of natural gas, whereby said undesired component may be taken up by the amine;
    amine transport means for supplying amine to said amine inlet;
    tapping means disposed intermediate said amine inlet and said amine outlet for withdrawing from said column a sample of liquid amine bearing the undesired component;
    an optical analyzer, including a high pressure, high temperature optical absorption cell in communication with said tapping means, for generating a signal indicative of the content in the amine of the undesired component; and
    regulating means for varying a flow rate of amine in said amine transport means and to said amine inlet of said absorption column.

2. Apparatus according to claim 1, wherein said optical absorption cell comprises two elongated quartz cylinders and means for adjusting the relative positions of said quartz cylinders to provide an adjustable spacing therebetween, said spacing defining an optical trajectory of said absorption cell.

3. Apparatus according to claim 2, wherein said quartz cylinders are circular cylinders having planar distal ends and said absorption cell comprises:
    a main body;
    first and second substantially cylindrical elongated bodies mounted on said main body and having cylindrical openings formed therein, distal ends of said substantially cylindrical bodies being bevelled, said quartz cylinders being respectively disposed in said cylindrical openings of said substantially cylindrical bodies, external diameters of said quartz cylinders corresponding to diameters of said cylindrical openings of said substantially cylindrical bodies;
    first and second sockets threaded onto said distal ends of said first and second substantially cylindrical bodies;
    a bevelled olytetrafluoroethylene joint wedged between each said socket and corresponding quartz cylinder, the bevels of said joints being wedged against said beveled of said substantially cylindrical bodies;
    first and second bases threaded onto said main body and respectively extending toward and beyond said distal ends of said quartz cylinders; and first and second seals respectively being sealingly engaged between said first and second bases and said distal ends of said quartz cylinders.

4. An adjustable optical absorption cell for making an optical measurement of a flowing material having high temperature and pressure comprising:
- a main body having inlet means and outlet means for receiving and discharging the material being measured;
- first and second elongated quartz cylinders mounted in said main body, there being a spacing between said quartz cylinders defining an optical trajectory of said absorption cell;
- first and second substantially cylindrical elongated bodies mounted on said main body and having cylindrical openings formed therein, distal ends of said substantially cylindrical bodies being bevelled, said quartz cylinders being respectively disposed in said cylindrical openings of said substantially cylindrical bodies, external diameters of said quartz cylinders corresponding to diameters of said cylindrical openings of said substantially cylindrical bodies;
- first and second sockets threaded onto said distal ends of said first and second substantially cylindrical bodies;
- a bevelled polytetrafluoroethylene joint wedged between each said socket and corresponding quartz cylinder, the bevels of said joints being wedged against said bevels of said substantially cylindrical bodies, wherein said spacing between said quartz cylinders may be adjusted by loosening at least one of said sockets and then moving at least one of said quartz cylinders;
- first and second bases threaded onto said main body and respectively extending toward and beyond distal ends of said quartz cylinders; and
- first and second seals respectively being sealingly engaged between said first and second bases and said distal ends of said quartz cylinders.

* * * * *